(12) United States Patent
Bode (10) Patent No.: US 11,176,846 B2
(45) Date of Patent: Nov. 16, 2021

(54) DENTAL SIMULATION MACHINE

(71) Applicant: Nissin Dental Products Inc., Kyoto (JP)

(72) Inventor: Dyon Bode, Zegveld (NL)

(73) Assignee: Nissin Dental Products Inc., Kyoto (JP)

(*) Notice: Subject to any disclaimer, the term of this patent is extended or adjusted under 35 U.S.C. 154(b) by 432 days.

(21) Appl. No.: 16/083,105

(22) PCT Filed: Mar. 9, 2017

(86) PCT No.: PCT/EP2017/055615
§ 371 (c)(1),
(2) Date: Sep. 7, 2018

(87) PCT Pub. No.: WO2017/153551
PCT Pub. Date: Sep. 14, 2017

(65) Prior Publication Data
US 2019/0096285 A1 Mar. 28, 2019

(30) Foreign Application Priority Data

| Mar. 10, 2016 | (GB) | ................................... 1604115 |
| Mar. 10, 2016 | (GB) | ................................... 1604155 |
| Mar. 11, 2016 | (GB) | ................................... 1604240 |
| Mar. 2, 2017 | (WO) | ............... PCT/EP2017/054959 |
| Mar. 7, 2017 | (WO) | ............... PCT/EP2017/055339 |

(51) Int. Cl.
*G09B 23/28* (2006.01)
*A61B 34/10* (2016.01)

(52) U.S. Cl.
CPC ............ *G09B 23/283* (2013.01); *A61B 34/10* (2016.02)

(58) Field of Classification Search
CPC ....... G09B 23/28; G09B 23/283; G09B 23/32
USPC ........................................... 434/263
See application file for complete search history.

(56) References Cited

U.S. PATENT DOCUMENTS

| 3,943,629 | A | * | 3/1976 | Ueno | ................... G09B 23/283 |
| | | | | | 434/263 |
| 6,088,020 | A | * | 7/2000 | Mor | ....................... G06F 3/016 |
| | | | | | 318/628 |
| 7,249,952 | B2 | * | 7/2007 | Ranta | ................... G09B 23/283 |
| | | | | | 434/263 |
| 8,716,973 | B1 | | 5/2014 | Lammertse | |
| 10,504,386 | B2 | * | 12/2019 | Levin | ................... G06F 3/0481 |

(Continued)

FOREIGN PATENT DOCUMENTS

| CN | 101719322 A | 6/2010 |
| CN | 203217859 U | 9/2013 |
| EP | 2988289 A1 | 2/2016 |
| JP | 2013105083 A | 5/2013 |

OTHER PUBLICATIONS

Brian Tse et al, "Design and Development of a Haptic Dental Training System—hapTEL", EuroHaptics 2010, Part II, LNCS 6192, pp. 101-108, 2010. (Year: 2010).*

(Continued)

*Primary Examiner* — Kurt Fernstrom
(74) *Attorney, Agent, or Firm* — Hodgson Russ LLP (57) ABSTRACT

A dental simulation machine including a support having a support surface for engagement by a finger of a user to support a hand of the user, the support surface being moveable between a plurality of positions.

18 Claims, 7 Drawing Sheets

(56) References Cited

U.S. PATENT DOCUMENTS

| | | | |
|---|---|---|---|
| 10,540,910 B2* | 1/2020 | Eid | G09B 23/283 |
| 10,695,150 B2* | 6/2020 | Kopelman | G16H 30/20 |
| 2004/0091845 A1* | 5/2004 | Azerad | G09B 23/283 |
| | | | 434/263 |
| 2006/0019228 A1* | 1/2006 | Riener | G09B 23/283 |
| | | | 434/263 |
| 2006/0252020 A1* | 11/2006 | Poitras | G09B 23/283 |
| | | | 434/263 |
| 2010/0311028 A1 | 12/2010 | Bell, III et al. | |
| 2014/0356835 A1* | 12/2014 | Montalbano | G09B 23/30 |
| | | | 434/263 |
| 2015/0264339 A1 | 9/2015 | Riedel | |
| 2018/0210553 A1* | 7/2018 | Banerjee | G06F 3/011 |

OTHER PUBLICATIONS

Tse et al., "Design and Development of a Haptic Dental Training System—hapTEL," Network and Parallel Computing, Springer International Publishing, Jul. 8, 2010, pp. 101-108.

Wang et al., "iDental: A Haptic-Based Dental Simulator and Its Preliminary User Evaluation," IEEE Transactions on Haptics, vo. 5, No. 4, Oct. 1, 2012, pp. 332-343.

Wang et al., "Survey on multisensory feedback virtual reality dental training systems," European Journal of Dental Education, Nov. 7, 2015, pp. 248-260.

Yoshida et al., "Development of a multi-layered virtual tooth model for the haptic dental training system," Dental Materials Journal, vol. 30, No. 1, Jan. 1, 2011, pp. 1-6.

\* cited by examiner

DENTAL SIMULATION MACHINE

FIELD OF THE INVENTION

The present invention relates to a dental simulation machine.

BACKGROUND TO THE INVENTION

Machines to simulate dentistry techniques for training purposes are known and include, for example, the Simodont machine manufactured by the applicant. These machines implement virtual reality technology to allow a student to practice various dentistry procedures. The simulation machines generally comprise a display screen which outputs 3D images for viewing by the user wearing 3D glasses. Positioned below the display screen is at least one hand piece (e.g. a physical simulated dentist tool) which is fixed to the machine by a mechanism comprising a series of linkages and electric motors. The relative position of the hand piece (as it is moved by the user) and the force applied by a user is measured as the user conducts a dentistry operation (for example, drilling into a tooth) on a virtual 3D model of a tooth, set of teeth or jaw. The hand piece simulates a dentist's drill and provides haptic feedback to the student as the student performs their drilling.

Dental simulation machines provide a simulation environment for trainee dentists before they are required to perform the same techniques on a real, rather than a virtual, tooth. Patient safety is very important. The more realistic the training environment the smoother the student's transition from practicing on the dental simulation machine to performing dentistry on a real patient.

Typically, the 3D model is artificially constructed. Different models are designed for different training requirements and situations—for example, a particular model may be of a chipped tooth (which the student is required to fix in a simulated training scenario). Other models may exhibit other characteristics or combinations of characteristics according to the needs of dentistry training programs.

An example of a supporting platform for training tactility in a virtual/actual dentistry operation is described in Chinese patent publication number CN101719322A. The supporting platform described in CN101719322A includes a lower tooth assembly having a ring member in which a user's index finger is inserted. The portion of a user's index finger having the proximal phalanx (the portion of the index finger a ring would sit on) is held within the ring member and the inner surface of the ring member supports the ring portion of the user's index finger. The ring member is mounted on the lower tooth assembly via a piston and locating pin, and thus the ring member is spaced apart from a plane defined by the tooth assembly. The inner surface of the ring member is positioned significantly above the plane defined by the tooth assembly.

SUMMARY OF THE INVENTION

According to one aspect of the present invention there is provided a dental simulation machine including a support having a support surface for engagement by a finger of a user to support a hand of the user, the support surface being moveable between a plurality of positions.

The support surface may be an upper support surface. The support surface may form a top face of the support. The support surface may be an outer facing surface of the support. The support surface may be provided at an upper end of the support.

According to a further aspect of the present invention there is provided a dental simulation machine including a support having a support surface for engagement by a finger of a user to support a hand of user, the support surface having a support surface area of less than 250 mm$^2$, preferably less than 200 mm$^2$, preferably less than 150 mm$^2$, preferably less than 100 mm$^2$.

BRIEF DESCRIPTION OF THE FIGURES

The invention will be described with reference to the drawings in which.

DETAILED DESCRIPTION

Figure 1:
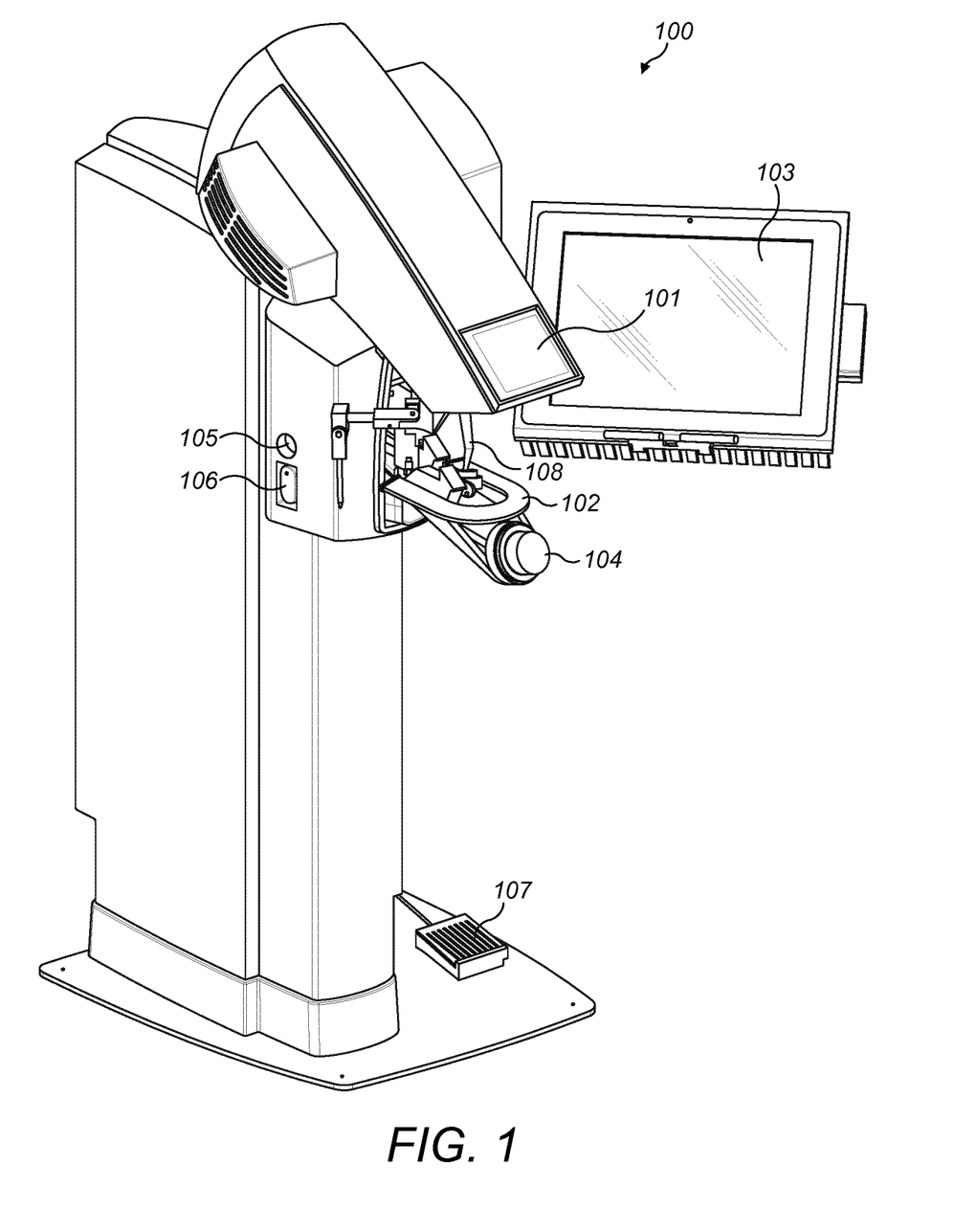
FIG. 1 is a perspective view of a dental simulation machine according to the present invention.

A dental simulation machine is shown generally at FIG. 1. The machine 100 is used by students of dentistry to practice dentistry using virtual reality technology. A student sits on a chair (not shown) facing viewing screen 101. Hand rest 102 defines, generally, an area in which the student operates a dentistry hand piece 108, such as a dentist's drill. Power button 105 provides machine on/off functionality and height adjustment switch 106 allows the user to adjust the height of a position of the machine 100, including hand rest 102 and viewing screen 101. Viewing screen 101 displays virtual 3D moving images whose movements correspond with movement of a hand piece 108 (which generally resides within area of hand rest 101) by a student. The student views the images on viewing screen 101 wearing passive 3D glasses. Mouse 104 allows the user of the machine to adjust the relative position and orientation of the images on viewing screen 101 in three dimensions. Foot pedal 107 facilitates control of operation of a simulated drill (or other powered dentistry tool).

The machine 100 also comprises training screen 103 (which may be a touch sensitive screen) which is used by the student to access information relevant to their training, such as training programs, individual lessons, scoring and marking data, mentor comments, and to review previous training material. While a simulation process is being performed, the images displayed on viewing screen 101 are also output to training screen 103 to allow an onlooker to view the student's use of the machine.

When using certain dentistry tools when performing dentistry work on a patient, such as a dental mirror, the dentist simply holds the mirror in the appropriate place, the end of the mirror may rest on part of the patient's mouth, for example it may rest on the inside of the cheek of the patient and therefore may be steadied by the inside of the cheek.

However, certain other tools, for example a dentist's drill needs to be held by the dentist and manipulated by the dentist. When using the drill the dentist tends to find support for their hand within the patient's mouth close to where the burr is operating on the tooth in question. In particular, the dentist may rest a finger of the hand holding the dentist's drill on a tooth adjacent the tooth being worked on or on a gum, or on part of the jaw.

As will be appreciated, using an adjacent tooth or a gum or part of the jaw as a prop, or for support only provides such support over a small localised area.

Prior art dental simulation machines have provided relatively large relatively flat surfaces against which an operator of the dental simulation machine can rest their hand. However, such relatively large relatively flat surfaces are not representative of the inside of a patient's mouth.

The present invention provides a more realistic environment on a dental simulation machine by providing a relatively small support surface for engagement by a part of a finger, for example an end or a tip or an edge of an end or a tip of a little finger or a ring finger or a middle finger, of a user of the dental simulation machine. By supporting the end or the tip of the finger of the user, the hand of the user is in turn supported. Such a discreet relatively small support of the dental simulation machine provides a more realistic environment when training. In particular, the support surface may be of a size similar to the surface of a tooth of a patient which a dentist might use to prop off when performing on a patient. The support surface may be of a size similar to a part of a gum or a part of a jaw which the dentist might use to prop off when performing on a patient.

Thus the support surface may have a support surface area of less than 250 mm², or less than 200 mm², or less than 150 mm², or less than 100 mm².

Figure 3:
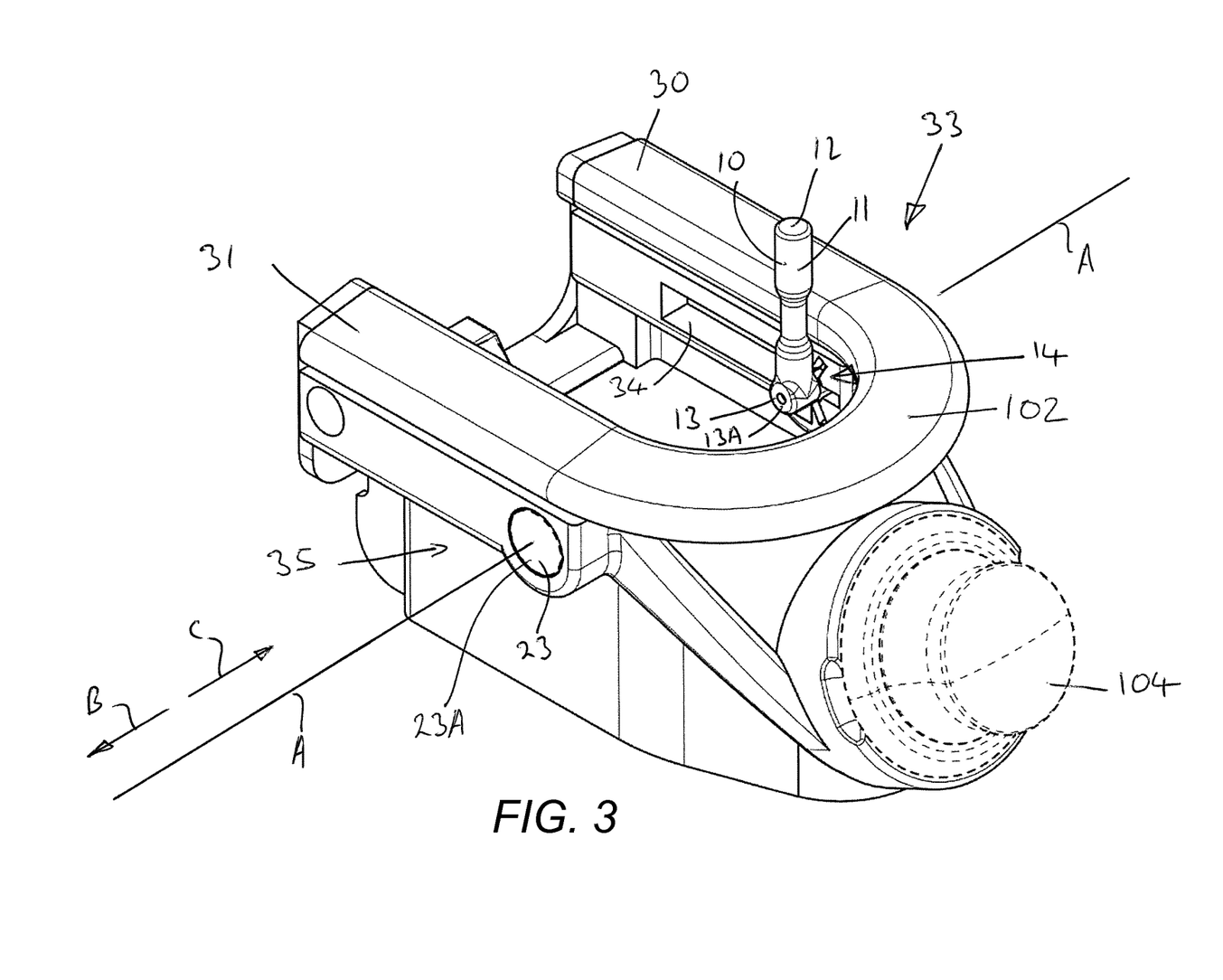
FIG. 3 is an isometric view of part of the dental simulation machine of FIG. 1 with a support in a first position.
Figure 4:
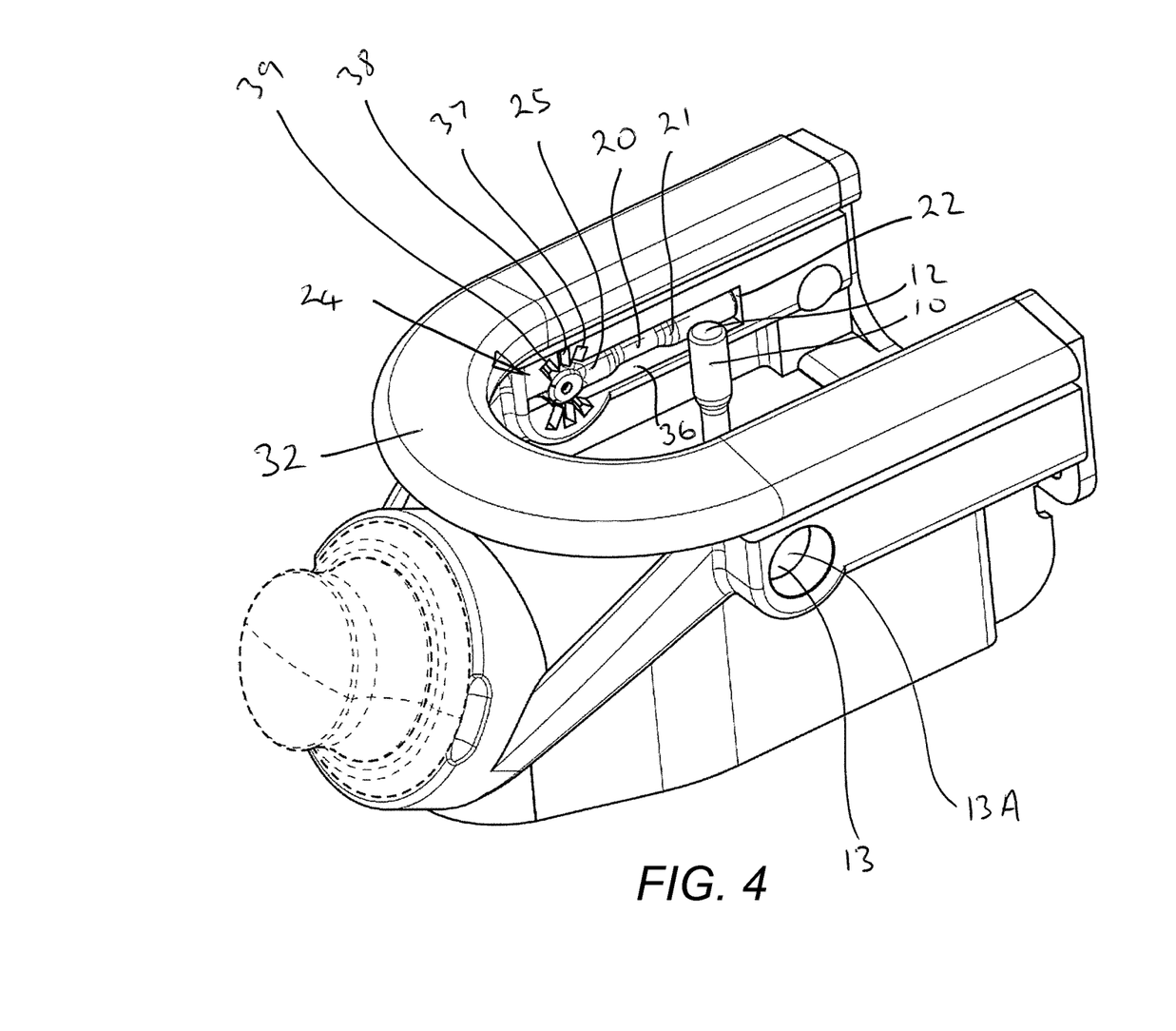
FIG. 4 is an alternative isometric view of FIG. 3.
Figure 5:
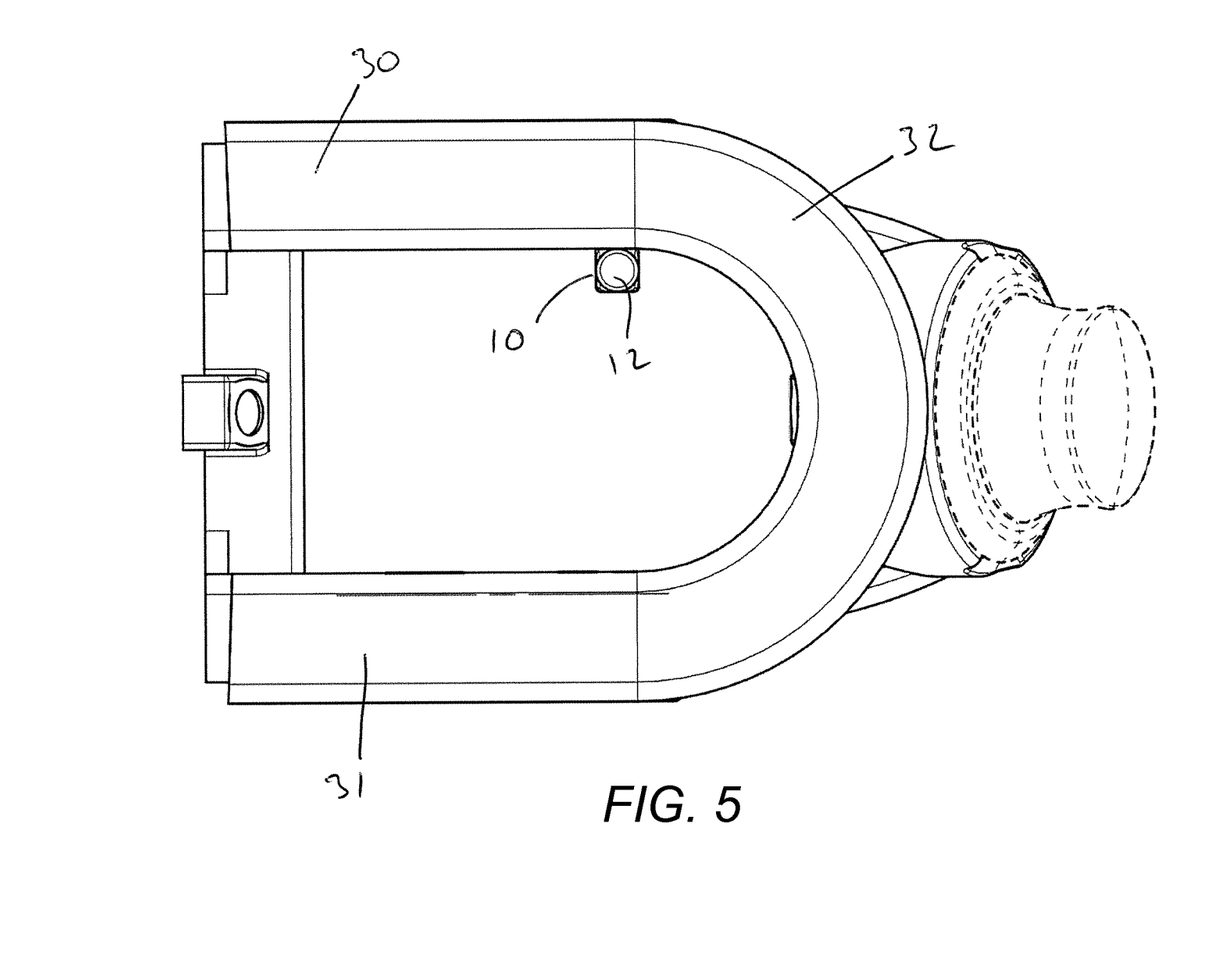
FIG. 5 is a plan view of FIG. 3.

With reference to FIGS. 3, 4 and 5 there is shown the hand rest 102 together with support 10. The hand rest 102 is generally U-shaped having a first arm 30 connected to a second arm 31 by an arcuate section 32. The support 10 is connected to the first arm 30 at region 33. The first arm 30 includes a recess 34.

A further support 20 is connected to the second arm 31 at region 35. The second arm 31 includes a recess 36.

Support 10 comprises a generally elongate body 11 having an upper support surface 12 at an end thereof. In other words, the support surface 12 is provided on a top face of the support 10. The support surface 12 provides an outer facing support surface at an upper end of the support 10. The further support 20 includes a corresponding generally elongated body 21 with a further upper support surface 22 at an end thereof. In other words, the support surface 22 is provided on a top face of the support 20. The support surface 22 provides an outer facing support surface at an upper end of the support 20.

The support 10 is pivotally mounted via a pivot 13 to the hand rest 102 at region 33.

The further support 20 is pivotally mounted via a pivot 23 to the hand rest 102 at region 35.

Figure 6:
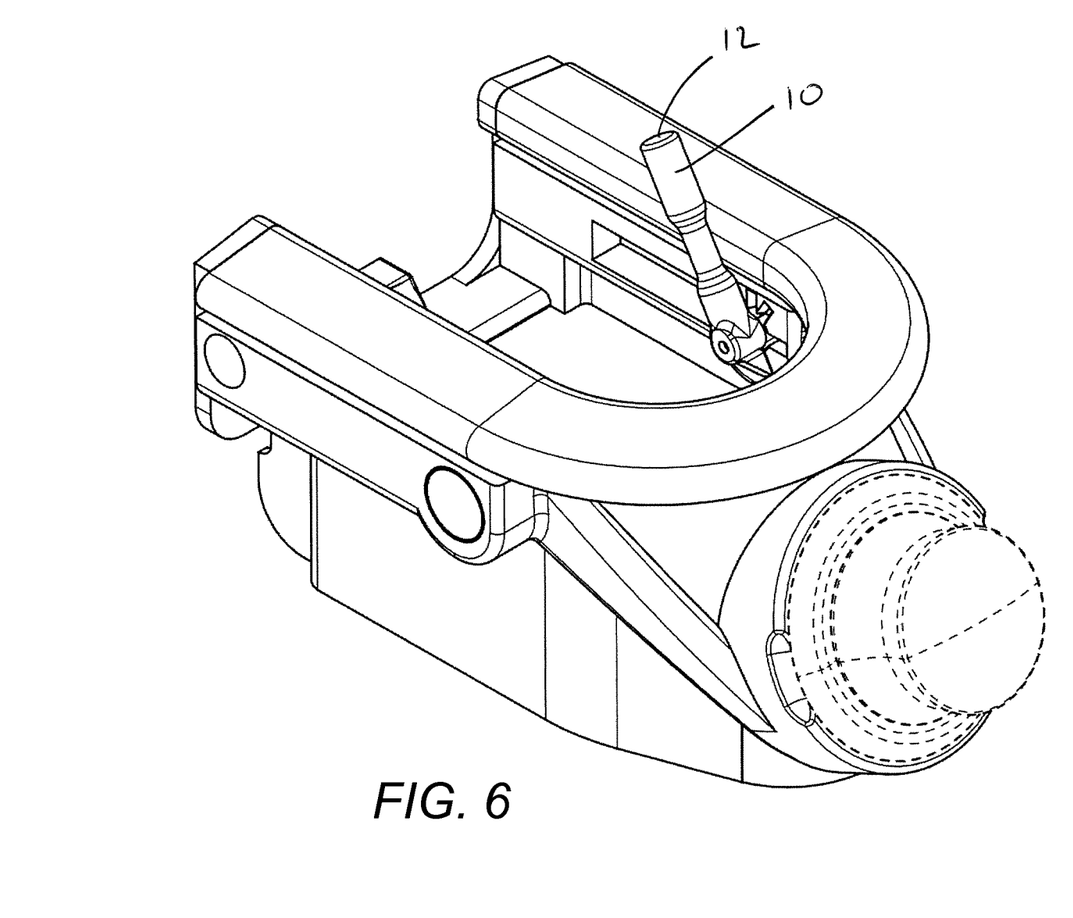
FIG. 6 is an isometric view similar to FIG. 3 with the support in an alternative position.
Figure 7:
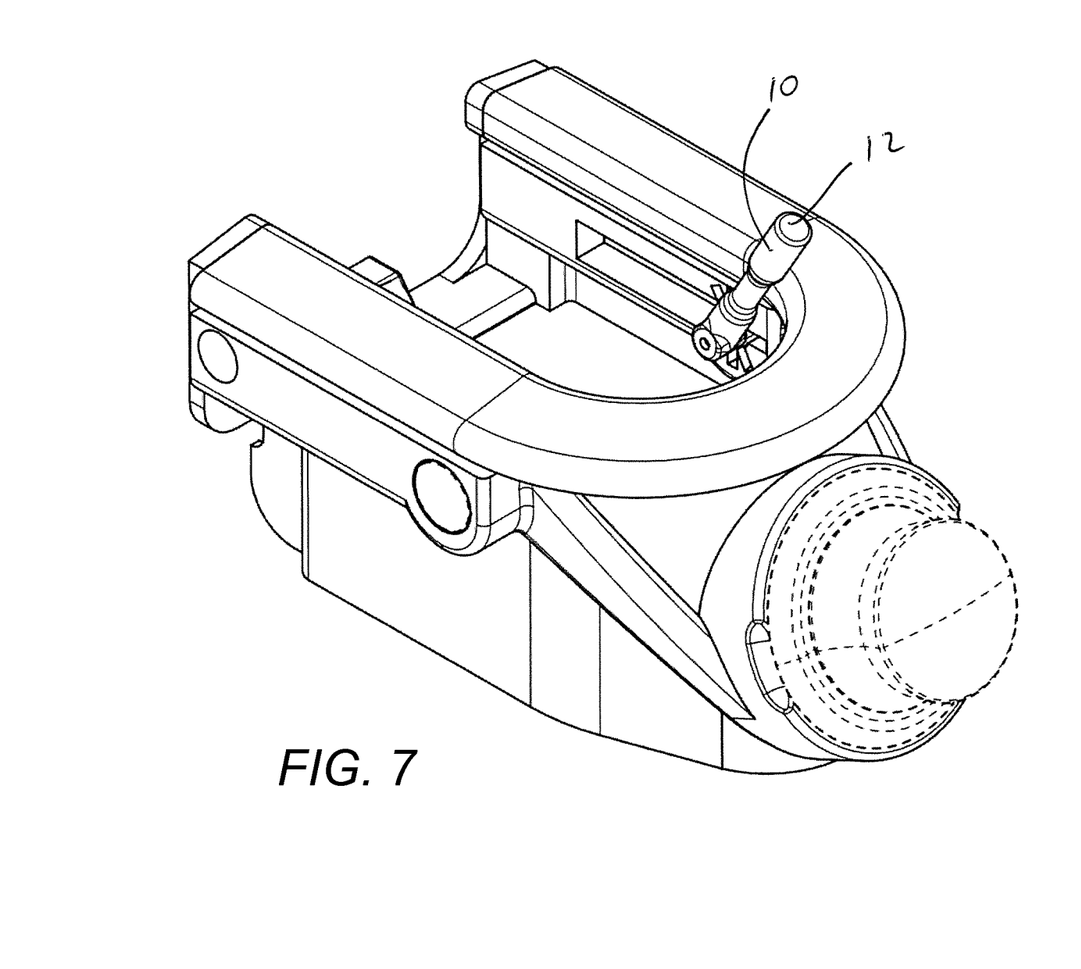
FIG. 7 is an isometric view similar to FIG. 3 with the support in an alternative position.

A detent 14 is operable to hold the support 10, and hence the support surface 12 in each of the deployed positions shown in FIG. 4, 6, 7 and a stored position (not shown in respect of support 10).

A detent 24 is operable to hold the further support 20, and hence the further support surface 22 in a plurality of deployed positions not shown but corresponding to those of support 10 shown in FIGS. 4, 6 and 7 and also in a stored position as shown in FIG. 4.

The detent 24 includes a rib or ribs (not shown) on the second end 25 of the generally elongate body which selectively engage in recesses 37, 38 or 39 to enable the further support 20 to be held in any one of the three deployed positions corresponding to the deployed positions of support 10 shown in FIGS. 4, 6 and 7. The detent also holds the further support 20 in the stored position as shown in FIG. 4.

The pivot 23 includes a pivot pin 23A having an axis A about which the further support 20 can rotate. The generally elongate body 21 is biased by a bias device (for example a spring not shown) in a first direction B. The bias device ensures that the detent keeps the further support 20 in either the stored position or any of the deployed positions as appropriate. The detent can be disengaged by moving the further support 20 in a direction opposing the spring, i.e. in the direction of arrow C, thereby disengaging the detent and allowing the further support to move to an alternate position.

As can be seen from FIG. 4, the further support 20 is mounted on an inside of the U-shape. As best seen from FIG. 3 the pivot pin 23A is accessible from the outside of the U-shape. In particular the user presses on the pivot pin 23A in the direction of arrow C with his or her finger to disengage the detent to allow the further support 20 to be moved to a desired position.

The support 10 also includes a pivot pin 13A having an axis (in this case the same axis A as pivot pin 23A). Accordingly, movement of support 10 between the three deployed positions shown in FIGS. 4, 6 and 7 and the stored position (not shown) is similar to that of movement of the further support 20 between its corresponding positions.

Figure 2:
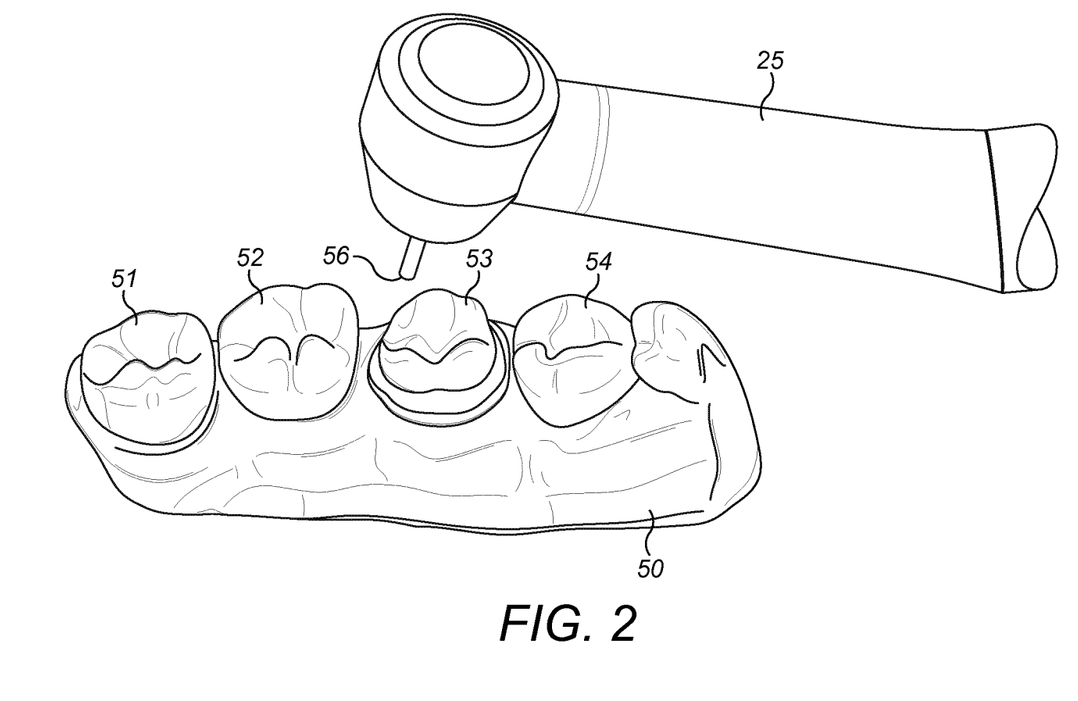
FIG. 2 is an example of what a user of the dental simulation machine might see through a display screen.

Turning to FIG. 2, this shows a view of what the user of the dental simulation machine 10 might see through the viewing screen 101. The user will be able to see a virtual simulated gum 50 with virtual simulated teeth 51, 52, 53 and 54. The user will also be able to see a virtual simulated drill 55 having a virtual simulated drill burr 56. As will be appreciated the virtual simulated features shown in FIG. 2 represent the equivalent features on an actual patient and an equivalent drill and burr used by an actual dentist.

The dental simulation machine includes a hand piece in the form of a physical simulated dentist's tool for example a physical simulated drill (108) which, when grasped by a user of the dental simulation machine will feel to that user like an actual drill. A user of the dental simulation machine may grasp or hold the hand piece 108 like a pen, with the hand piece 108 held between the user's thumb and index finger (forefinger). The hand piece 108 may be rested on the elongate edge of the user's middle finger. A simulated dentist's tool provides haptic feedback to the student or the like as the student performs their drilling.

In an example, the support surface 12 is a physical simulated part of a patient. It is relatively small. In particular its size is such that it is only possible for a student to rest part of a finger, for example an end or a tip or an edge of an end or a tip of a finger such as a little finger or a ring finger or a middle finger, on the support surface 12 and this better represents the type of support available for a dentist when operating on a patient. For example, the support surface 12 is of a size similar to that of a patient's tooth which the dentist may use to prop against. Whilst an entire gum of a patient is significantly bigger than the support surface 12, in view of the limited space available in a patient's mouth, and in view of the size of the dentist's hand, it is not possible for the dentist to support their hand off the entire gum line of a patient. Rather in practice it is found that only relatively small parts of the gum line can be used by a dentist to support their hand. In practice, a dentist may only be able to rest an end or a tip or an edge of an end or a tip of the little finger or an end or a tip or an edge of an end or a tip of the ring finger or an end or a tip or an edge of an end or a tip of the middle finger against a correspondingly small part of the gum line and accordingly the support surface 12 is a good physical representation of that part of the gum line against which a dentist might rest a part, in particular an upper part, for example an end or a tip or an edge of an end or a tip, of a finger, for example a little finger or a ring finger or a middle finger for support.

The row of teeth on a patient's lower jaw define a plane. When a dentist drills a hole in one of the teeth in the row, he or she may (as described above) rest a part of his or her little finger or ring finger or middle finger on another of the patient's teeth in the row. Before drilling, the tip of the drill starts out at or slightly above the plane defined by the row of the patient's teeth. During drilling, the tip of the drill drills down below the plane defined by the patient's teeth. During drilling, the drill may drill into the patient's tooth by a desired amount, typically 0.5 to 1.0 centimetres, i.e. the drill may extend below the plane of the patient's teeth by approximately 0.5 to 1.0 centimetres.

Similarly, the dental simulation machine provides a physical support surface 12 that simulates a tooth that is one of a virtual simulated row of teeth. The physical simulated tooth defines a virtual plane of the virtual simulated row of teeth. The user rests a part of his or her little finger or ring finger on the support surface 12. Prior to simulated drilling, the user holds a physical simulated drill (the hand piece 108) such that the virtual simulated burr 56 of the virtual simulated drill 55 visible by the user in the viewing screen 101 is at or slightly above the virtual plane defined by the support surface of the physical simulated tooth. During drilling, the simulated burr 56 of the simulated drill 55 extends below the virtual plane defined by the physical simulated tooth by approximately 0.5 to 1.0 centimetres according to the procedure that is simulated on the dental simulation machine, thus providing a more realistic environment on a dental simulation machine.

Note that whilst in the above examples the support surface 12 represents a physical simulation of part of a patient, it need not represent any part of the patient. Thus, there is a skill involved in learning to prop a hand against a relatively small feature by resting an end or a tip or an edge of an end or a tip of a little finger or a ring finger or a middle finger on a relatively small feature. This skill can be learnt by using support surface 12 without the need for support surface 12 to represent a part of the patient. Once the skill of propping a hand by resting an end or a tip of a finger off a small feature has been learnt, then the further skill of propping a hand by resting an end or a tip of a finger off a small feature positioned as found in a patient's mouth can be learnt by arranging the support surface to represent a physical simulation of a part of a patient.

Whether or not the support surface 12 represents a physical simulation of part of a patient, the support surface 12 may or may not be represented in a view as seen through the viewing screen 101 by the student.

However in a preferred embodiment, the support surface 12 may be represented in the view as seen through the viewing screen 101 by the student.

By way of example arranging the apparent position of the virtually simulated teeth and gum shown in FIG. 2 appropriately with respect to the hand rest 102, then the support surface 12 when positioned as shown in FIG. 7 represents a physical simulation of virtual tooth 54.

In this example, the virtual simulated gum and teeth are as shown in FIG. 2. The student holds the physical simulated drill (the hand piece, 108) in his/her right hand. The student may hold the physical simulated drill like a pen, with the physical simulated drill held between the thumb and index finger (forefinger) of the student's right hand. The hand piece may be rested on the elongate edge of the middle finger of the student's right hand. Accordingly, the virtual simulated drill 55 and burr 56 will appear as shown in FIG. 2. Under these circumstances a dentist operating on a patient might wish to rest the end or the tip of the little or small or ring or middle finger of their right hand on an actual tooth the equivalent of virtual simulated tooth 54 in order to drill into an actual tooth the equivalent of virtual simulated tooth 53. Under these circumstances the support 10 and support surface 12 would be positioned as per FIG. 7 so as to represent virtual simulated tooth 54 and hence the user of the dental simulation machine would be able to support the end or tip of his or her little or ring or middle finger on support surface 12 which would feel as if it were correctly positioned with respect to the other viewed components, in particular with respect to the virtual simulated drill 55, virtually simulated burr 56 and the virtually simulated tooth 53 being worked on.

In a further example, the user of the dental simulation machine may wish to work on virtual simulated tooth 53 but may wish to hold the physical simulated drill 108 in his/her left hand. The user may hold the physical simulated drill like a pen, with the physical simulated drill held between the thumb and index finger (forefinger) of the user's left hand. The hand piece may be rested on the elongate edge of the user's middle finger. Under these circumstances a dentist might want to prop the end or the tip of his/her little or small or ring or middle finger of his or her left hand on an actual tooth the equivalent of virtual simulated tooth 52. One option would be to reposition the virtual simulated features as shown in FIG. 2 such that the position of the support surface 12 as found in FIG. 7 now corresponds with virtual simulated tooth 52. Alternatively, the support 10 and hence support surface 12 can be moved to the position shown in FIG. 6 where the support surface 12 now corresponds to the position of virtual simulated tooth 52 and therefore provides a physical simulation of virtual simulated tooth 52.

If then the user of a dental simulation machine wishes to work on virtual simulated tooth 52 and hold the drill in his/her right hand, then either the support surface can remain in the same position (i.e. as per FIG. 6) and the model can be moved such that support surface corresponds with the virtual simulated tooth 53 or alternatively the model can remain in the same position and the support 10 and support surface 12 can be moved to the position shown in FIG. 4 wherein the support surface 12 corresponds with virtually simulated tooth 53.

In particular, it will be appreciated that by providing three deployed positions of support surface 12 which represents three physical simulations of three teeth allows for supporting of an end or a tip of a finger and hence a hand when working on any of four virtual simulated teeth. This saves having to move the model every time a different virtual simulated tooth is to be worked on.

The further support 20 and further support surface 22 enable simulation of the right hand side of a patient's jaw in a similar manner.

As will be appreciated, with the support 10 orientated as shown in FIG. 4, a student's finger may rest entirely on the top circular surface. For example, an end or a tip of a student's little or ring or middle finger may rest entirely on the top circular surface. With the finger rest orientated as shown in FIG. 6 then a student's finger may rest partially on part of the circular end surface and partially on part of the cylindrical surface immediately adjacent the circular end surface. For example, an edge of an end or a tip of a student's little or ring or middle finger may rest partially on part of the circular end surface and partially on part of the cylindrical surface immediately adjacent the circular end surface. With the support 10 position as shown in FIG. 7, then a student's finger may rest in part on part of the circular end of the support and in part on an opposite part of the cylindrical surface of the support 10 immediately adjacent the circular end surface. For example, an edge of an end or a tip of a student's little or ring or middle finger may rest in part on part of the circular end of the support and in part on an opposite part of the cylindrical surface of the support 10 immediately adjacent the circular end surface.

It will be appreciated that, with the hand piece of the dental simulation machine held or grasped like a pen, with the hand piece held between the user's thumb and index finger (forefinger), and the end or tip of the user's little finger supported on either support surface 12 or support surface 22, the hand piece can be moved in a full range of motion in the lateral, up-down and fore-aft directions.

However the support is orientated, and under all circumstances the student's finger, for example an end or a tip of the student's finger, rests on a relatively small area and this provides a more realistic dental simulation machine.

As will be appreciated, whether the support is orientated as in FIG. 4 or FIG. 6 or FIG. 7, the support surface is provided towards an end of the body.

The invention claimed is:

1. A dental simulation machine including a support having an outer facing support surface for engagement by a finger of a user to support a hand of the user, the support surface being moveable between a plurality of positions, wherein a detent is operable to hold the support surface in each of the plurality of positions, wherein the support is pivotally mounted by a pivot to enable the support surface to move between the plurality of positions and wherein the pivot includes a pivot axis and movement of the support surface in a first direction parallel to the pivot axis disengages the detent.

2. A dental simulation machine as defined in claim 1 wherein the plurality of positions includes a first position for engagement by a finger of the user to support the hand of a user in a first position and includes a second position for engagement by a finger of the user to support the hand of the user in a second position.

3. A dental simulation machine as defined in claim 2 wherein the plurality of positions includes a third position for engagement by a finger of the user to support the hand of the user in a third position.

4. A dental simulation machine as defined in claim 1 wherein the plurality of positions includes a stored position.

5. A dental simulation machine as defined in claim 1 wherein the support is pivotally mounted by a pivot to enable the support surface to move between the plurality of positions.

6. A dental simulation machine as defined in claim 1 wherein the support includes a generally elongate body with the support surface being provided at an end of the body.

7. A dental simulation machine as defined in claim 6 wherein the support is pivotally mounted by a pivot to enable the support surface to move between the plurality of positions and wherein the support surface is provided at a first end of the body and the pivot is provided proximate a second end of the body.

8. A dental simulation machine as defined in claim 1 wherein the support includes a generally elongate body with the support surface being provided at an end of the body and wherein the support body is biased in a second direction, opposite to the first direction, parallel to the pivot axis to engage the detent.

9. A dental simulation machine as defined in claim 1 wherein the support is mounted to a rest.

10. A dental simulation machine as defined in claim 9 wherein the support is pivotally mounted by a pivot to enable the support surface to move between the plurality of positions and wherein the support is pivotally mounted by the pivot to the rest.

11. A dental simulation machine as defined in claim 10 wherein the support is located on a first side of a region of the rest and a pivot pin of the pivot is accessible on a second side of the region of the rest to disengage the detent.

12. A dental simulation machine as defined in claim 9 wherein the plurality of positions includes a stored position and wherein the support is received in a recess of the rest when the support surface is in the stored position.

13. A dental simulation machine as defined in claim 9 wherein the rest is generally U-shaped having a first arm and a second arm.

14. A dental simulation machine as defined in claim 13 wherein the support is mounted to the first arm.

15. A dental simulation machine as defined in claim 14 further including a second support having a second support surface for engagement by a finger of a user to support a hand of the user, the second support surface being moveable between a second plurality of positions, wherein the second support is mounted to the second arm.

16. A dental simulation machine as defined in claim 15 wherein the support and/or the second support are mounted on an inside of the U-shape.

17. A dental simulation machine as defined in claim 1 including a viewing screen for viewing a virtual simulated model.

18. A dental simulation machine as defined in claim 17 wherein the virtual simulated model includes a representation of the support surface.

* * * * *